Figure 1:
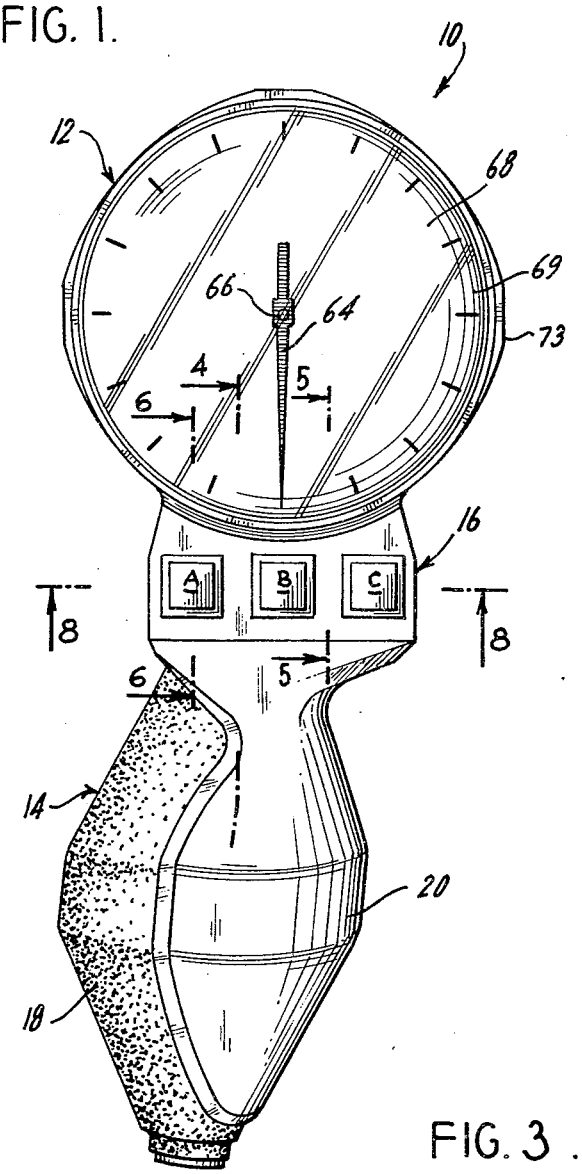

United States Patent [19]

Raczkowski et al.

[11] 3,954,099
[45] May 4, 1976

[54] SPHYGMOMANOMETER

[75] Inventors: Jan Raczkowski; Stefania Raczkowski, both of Long Beach, N.Y.

[73] Assignee: Propper Manufacturing Co., Inc., Long Island, N.Y.

[22] Filed: Feb. 8, 1974

[21] Appl. No.: 440,652

[52] U.S. Cl. .......................... 128/2.05 G; 137/556; 137/612.1; 251/122
[51] Int. Cl.² ......................................... A61B 5/02
[58] Field of Search ............... 128/2.05 G, 2.05 A, 128/2.05 C, 2.05 M, 2.05 N, 2.05 Q, 2.05 Z; 137/612.1, 556; 251/122

[56] References Cited
UNITED STATES PATENTS

| | | | |
|---|---|---|---|
| 2,630,796 | 3/1953 | Eksten, Jr. | 128/2.05 G |
| 2,934,061 | 4/1960 | Speelman | 128/2.05 G |
| 3,504,663 | 4/1970 | Edwards | 128/2.05 G |
| 3,508,537 | 4/1970 | Kahn et al. | 128/2.05 A |
| 3,613,668 | 10/1971 | Beck et al. | 128/2.05 G |
| 3,654,915 | 4/1972 | Sanctuary | 128/2.05 M |
| 3,823,707 | 7/1974 | Hayes | 128/2.05 G |
| 3,828,811 | 8/1974 | Natkanski | 137/556 |

Primary Examiner—Kyle L. Howell
Attorney, Agent, or Firm—Amster & Rothstein

[57] ABSTRACT

A sphygmomanometer in which individual valve mechanisms under control of a series of push buttons are provided to permit release of air from the sphygmomanometer cuff at approximate predetermined rates for proper diagnosis. The valve arrangement includes a safety release feature which prevents the buildup of excess pressure in the manometer.

7 Claims, 12 Drawing Figures

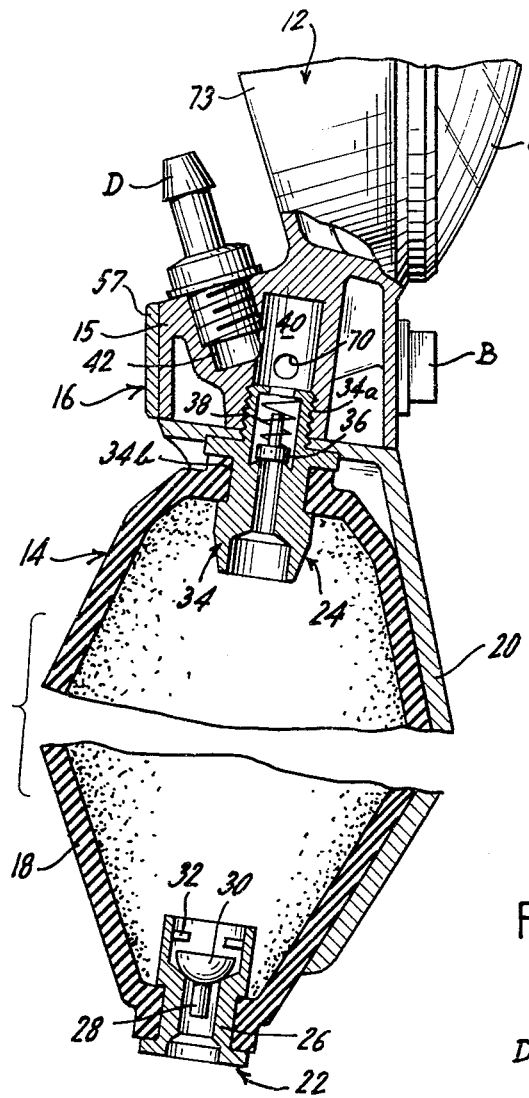
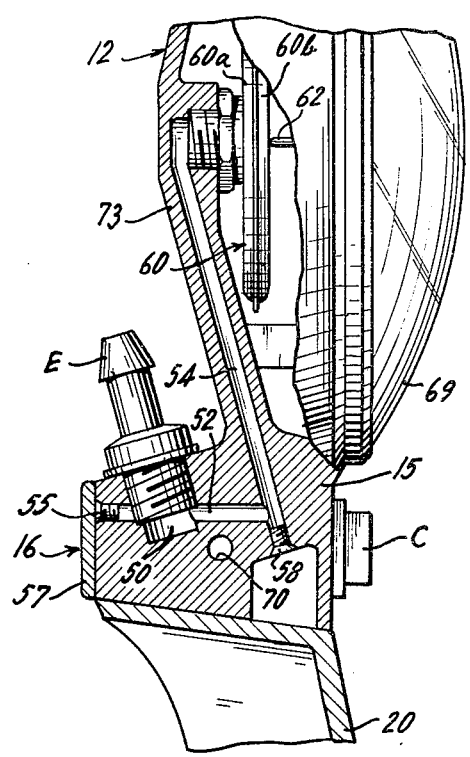
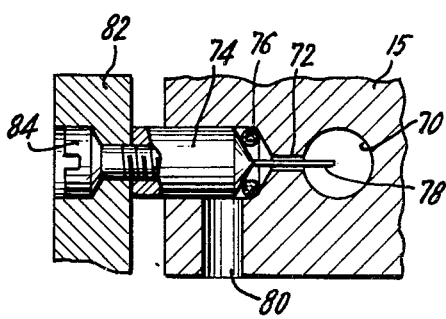
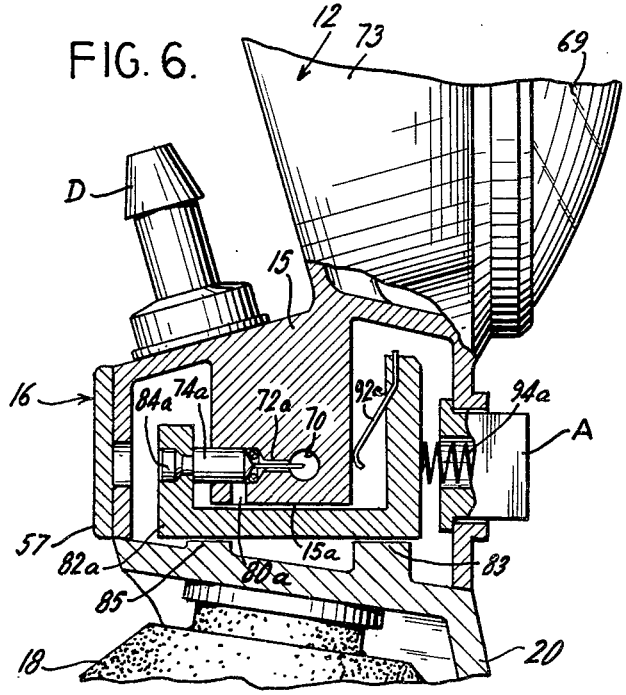

SPHYGMOMANOMETER

This invention relates generally to medical instruments and appliances and more particularly to a blood pressure measuring device conventionally known as a sphygmomanometer.

For purposes of general examination, human blood pressure is conventionally measured in the following manner: A cuff including an inflatable bladder is placed around the patient's upper arm. The cuff itself is substantially unyielding so that inflation of the bladder constricts the upper arm, tending to cut off the flow of blood in the vessels of the arm (the brachial artery). In practice, the cuff is inflated, usually with a flexible, hand-held bulb to a pressure of approximately 30 mm Hg (millimeters of mercury) above the point at which the patient's radial pulse in the brachial artery below the cuff disappears. The pressure in the cuff is continually monitored with an appropriate pressure-sensing device, usually an aneroid or mercurial manometer. The doctor then listens to the brachial artery with a stethoscope beneath the constriction of the cuff and slowly releases the pressure in the cuff. As the pressure falls, the doctor will first hear tapping sounds marking the return of pulsing arterial blood flow beneath the cuff. The pressure reading at the point where such pulses are heard for at least two consecutive beats constitutes the systolic blood pressure. The doctor continues to release air from the cuff until the tapping sounds become muffled by the flow of blood in the artery, at which point the doctor notes the diastolic pressure. These two measurements, systolic and diastolic pressure, constitute the conventional blood pressure indication.

To obtain accurate blood pressure readings, it is important that the cuff pressure be decreased at a steady, slow rate. Abrupt fluctuations in the rate of decrease make it difficult, if not impossible, to obtain accurate pressure readings, particularly when using an aneroid instrument. The American Heart Association, in a pamphlet entitled, "Recommendations for Human Blood Pressure Determination by Sphygmomanometers," suggests that for reading ordinary pressures, a rate of release of approximately 2 to 3 mm Hg per second be used. After measurement is complete, a quick release rate is desirable to permit convenient removal of the cuff.

Conventional sphygmomanometers employ a rotating valve of varying designs to release pressure from the cuff. While there are a variety of different specific valve constructions adapted to perform this function, most require the doctor to carefully regulate the valve opening to maintain the desired release rate. Accurate control of the release rate and the ability to sustain the release rate at a controlled slow rate of release requires considerable attention and dexterity and requires the doctor to develop a feel for the specific valve being used. A doctor picking up an instrument with which he is not intimately familiar may have difficulty controlling the release rate accurately.

Another problem with turn valves of this type is that they do not provide a safety pressure release, so that overpressurization of the cuff-manometer system may distort or rupture the manometer diaphragm, destroying the calibrated accuracy of the instrument.

It is thus an object of the present invention to make it easy for the physician to obtain controlled release of air from a sphygmomanometer cuff at an appropriate slow, steady rate. A related object of the invention is to provide a sphygmomanometer in which the doctor can release pressure from the cuff at substantially the same rate time after time.

A further object of the invention is to provide a sphygmomanometer in which the manometer cannot be damaged by overpressurization.

In accomplishing these and other objects in accordance with the present invention, applicant's sphygmomanometer includes an inflatable cuff, a manometer adapted to reflect the pressure within the cuff, an inflation bulb, and a valve system including a plurality of individual pre-set valves which permit release of air from the cuff at selected rates under control of a series of push buttons.

Figure 2:
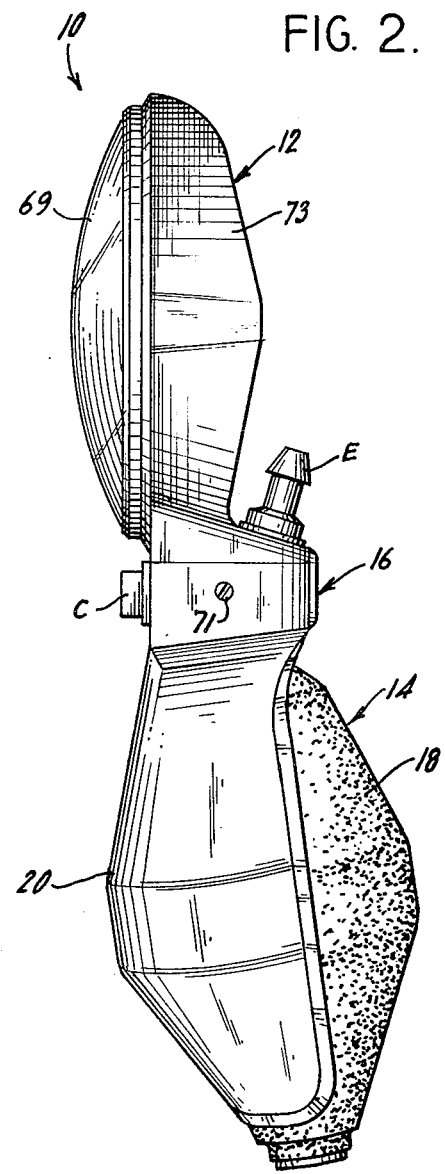
Figure 3:
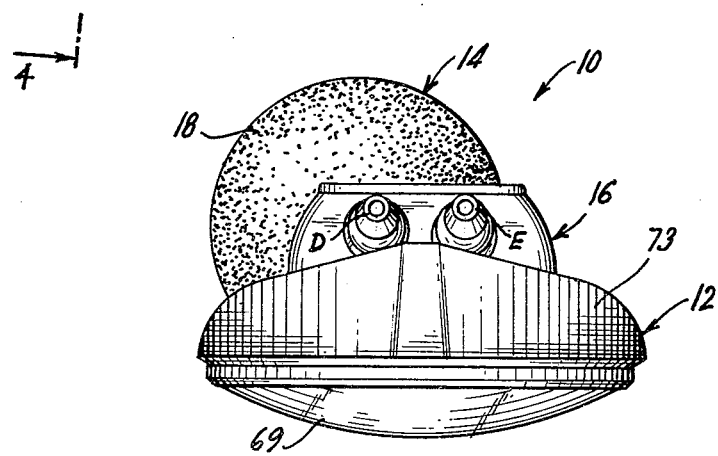
Figure 8:
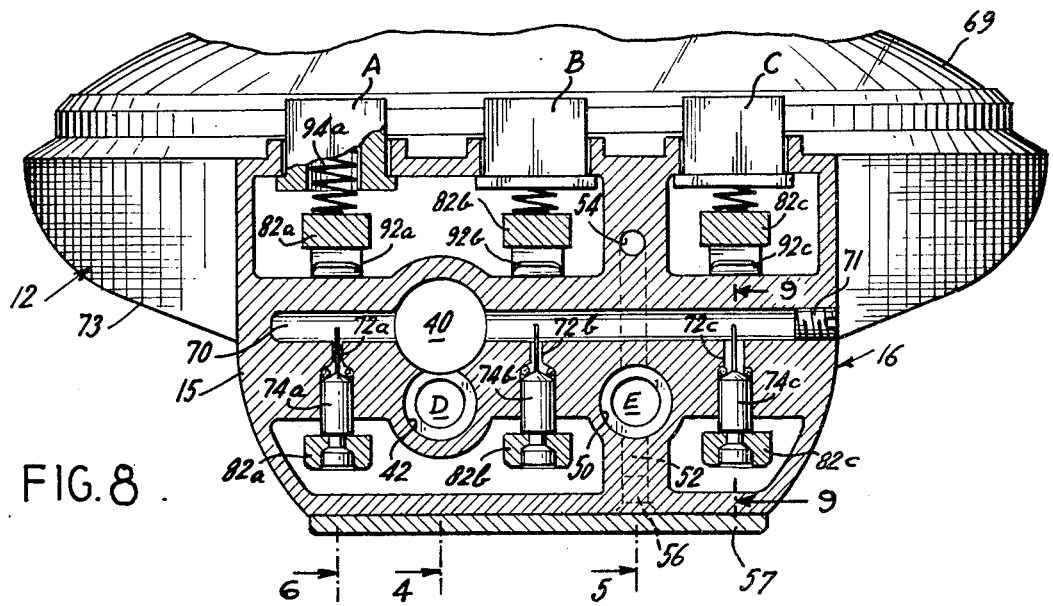
Figure 9:
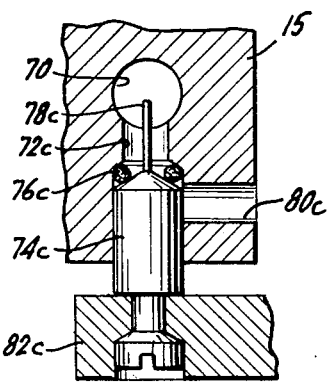
Figure 10:
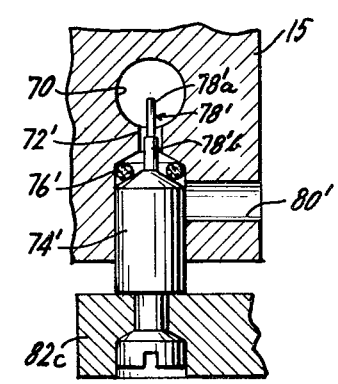
Figure 11:
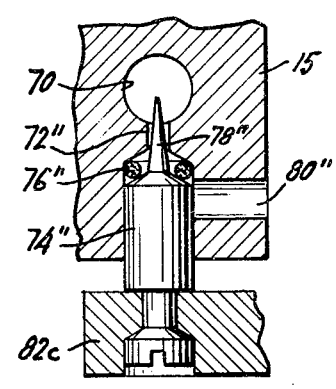
Figure 12:
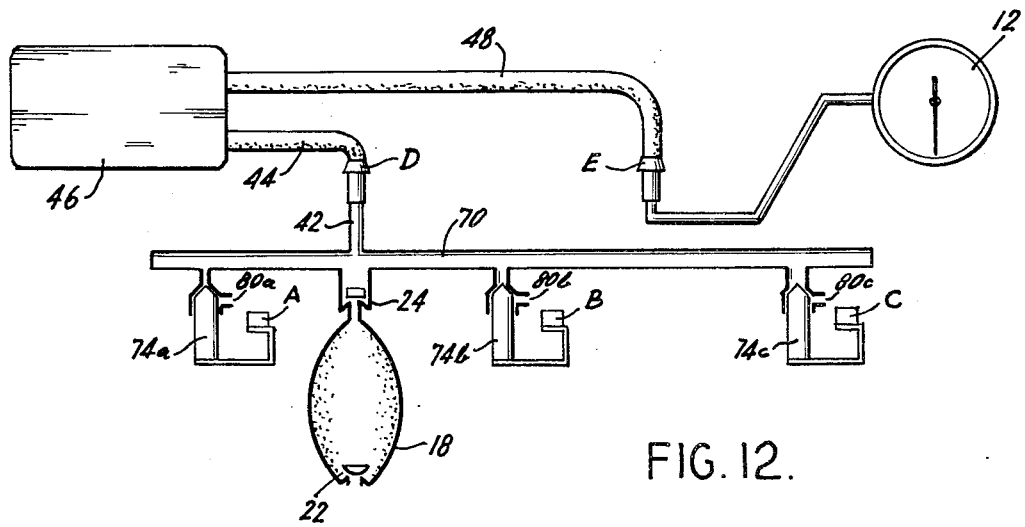

Further objects, features and advantages of the present invention will be more fully appreciated by reference to the following detailed description of the presently preferred embodiment of the invention, when taken in conjunction with the appended drawings, wherein:

FIG. 1 is a front view of the sphygmomanometer;
FIG. 2 is a side view of the sphygmomanometer;
FIG. 3 is a top view of the sphygmomanometer;
FIG. 4 is a cross-sectional view taken along line 4—4 in FIG. 1 looking in the direction of the arrows;
FIG. 5 is a cross-sectional view taken along line 5—5 in FIG. 1 looking in the direction of the arrows;
FIG. 6 is a cross-sectional view taken along line 6—6 in FIG. 1 looking in the direction of the arrows;
FIG. 7 is an enlarged sectional view of one of the valve elements of the sphygmomanometer;
FIG. 8 is a cross-sectional view taken along line 8—8 in FIG. 1 looking in the direction of the arrows, with the position of the cross-sectional view of FIGS. 4, 5 and 6 being indicated for clarity;
FIG. 9 is an enlarged sectional view taken along line 9—9 in FIG. 8;
FIG. 10 is an enlarged sectional view of a modified valve arrangement;
FIG. 11 is an enlarged sectional view of a further modified valve arrangement; and
FIG. 12 is a functional diagram of the sphygmomanometer system.

FIGS. 1, 2 and 3 generally show the exterior of the sphygmomanometer 10 including a pressure gauge or manometer portion 12, an inflation bulb portion 14 and a valve portion 16. The manometer inflation bulb and valve elements of applicant's sphygmomanometer are unified in a single coordinated structure for ease of handling and operation. It will be appreciated that the appended drawings do not show (except for the functional diagram of FIG. 12) the inflation cuff nor the tubes for connecting the cuff to the body of the instrument. The design of such cuffs is well known to those skilled in the art. Sphygmomanometer 10 does include an inflation-deflation nipple D and a pressure-reading nipple E on the rear of the valve section of the instrument. The connection of these valves to a conventional cuff is well known in the art, and will be described in somewhat further detail below.

As shown in FIGS. 1, 2 and 3, the inflation section 14 includes an inflation bulb 18 which is preferably made of a resilient rubber material which can be readily compressed and which quickly returns to its original shape when released. The bulb configuration includes two opposed conical sections with an intermediate flat section and is adapted to fit comfortably into the doctor's hand. In addition, the bulb is designed to have the maximum volume area in the region of the third and fourth fingers of the doctor's hand, which are capable of exerting the greatest gripping force. The bulb section also includes a rigid bulb shield 20 which is similarly contoured to fit the doctor's hand and provides a solid backing against which the bulb can be compressed. Applicant has found that this bulb/bulb shield arrangement permits the doctor to inflate the cuff more rapidly than other arrangements and with less hand fatigue.

Preferably, in applicant's sphygmomanometer, the bulb shield 20 comprises a molded element and the chassis of the valve section 16 and the case of the manometer section 12 comprises a second molded section. It is to be understood, however, that numerous other methods of construction are possible.

The internal operation of the bulb will be appreciated by reference to the lower portion of FIG. 4 where the bulb is shown in cross section along with its air input valve 22 and air output valve 24. Valves 22 and 24 are coordinated such that on squeezing bulb 18, air is driven upwardly through valve 24, through a path to be described hereinafter to nipple D which is adapted for connections to the cuff. During this portion of the bulb cycle, intake valve 22 is closed, so that all air in the bulb is driven through nipple D. Upon release of the bulb, valve 24 closes, preventing the return of air under pressure from the cuff to the bulb while valve 22 is open to incoming air which fills the bulb through valve 22 as the bulb returns to its original shape.

Various different valve configurations may be used in bulb 18 in accomplishing this cycle. As shown in FIG. 4, valve 22 includes a valve chassis 26 having a bore through its center, with the bore being adapted to provide a seat for a half ball valve closing member 30. Half ball member 30 includes a guide pin 28 and is retained in chassis 26 by retaining lugs 32. It will be appreciated that air can be drawn into the bulb through the central bore and around half ball 30, but that compression within the bulb locks half ball 30 against the seat provided in chassis 26, closing the valve and preventing air from escaping during this portion of the cycle.

Valve 24 similarly includes a valve chassis 34 and a central bore defining an air channel through the chassis. The outer configuration of valve chassis 34 is designed to include a threaded upper portion 34a which is received within a corresponding thread in the interior of valve section 16. If needed, a sealing washer (not shown) may be provided around threaded section 34a between bulb shield 20 and the valve section 16. The valve chassis lower portion 34b defines an annular channel (shown in cross-section in FIG. 4) which is adapted to tightly receive a similarly dimensioned portion of the wall of bulb 18 such that the entire valve chassis 34 can be snapped fit into the upper aperture of bulb 18 in an apparent manner. Valve 24 includes a closing member 36 which is urged downwardly by spring 38 against a seat provided in chassis 34, thereby closing the valve bore to the passage of air. Air under sufficient pressure from within bulb 18 will compress spring 38, permitting a flow of air from the bulb to nipple D while air return during inflation of the bulb is prevented.

Note that valve 24 is an integral, removable unit which can be unscrewed from valve section 16 and disengaged from bulb 18 for independent testing and evaluation. This differs sharply from prior inflation valves which conventionally form an integral part of the valve mechanism and cannot be removed intact for testing.

To complete the path of air to the cuff, it will be apparent from FIG. 4 that air pressed out of bulb 18 passes through valve 24 to chamber 40 in the valve chassis 15 of valve section 16 of the sphygmomanometer. Chamber 40 opens into chamber 42 which also receives nipple D which is threaded into chamber 42 during manufacture. The interconnection between interior chambers 40 and 42 can be seen more clearly in the sectional view of FIG. 8. Nipple D is of a wellknown type including a frustoconical tip section adapted to receive and form a substantially airtight connection with the flexible rubber hose. It will be appreciated that in the preferred embodiment shown in the drawings, the valve section is a molded unit with interior chambers (such as chamber 42) drilled out. In the figures, the base of these chambers are shown flat, while in fact they might have sloped tips caused by the drill bit.

As is apparent from what has been said above, repeated squeezing of bulb 18 inflates the cuff through nipple D. The air pressure in the cuff is constantly monitored by manometer 12. The interconnection of the bulb cuff and manometer is shown in FIG. 12 which shows a section of flexible rubber tube 44 interconnecting nipples D and bladder 46 within the cuff. A second section of flexible tube 48 connects the bladder 46 with nipple E, which is interconnected to manometer 12. The interconnection of nipple E with manometer 12 will best be seen in FIG. 5.

Referring to FIG. 5, nipple E is embedded into a machined cavity 50 in the chassis 15 of valve section 16 during manufactured in a manner substantially identical to that previously described for nipple D. Chamber 50 communicates with a horizontal bore 52 which in turn communicates with an angled vertical bore 54 to create an air channel to the manometer mechanism. Horizontal bore 52 is machined into the valve chassis during manufacture and is thereafter closed with a closing screw 55. A back plate 57 is positioned over the rear of section 16 to hide the screw head and other apertures created during manufacture, such as aperture 56 in FIG. 6. Similarly, channel 54 is machined up from the bottom surface of section 16 and is closed with a screw 58. Channels 54 and 52 together with chamber 50 provide a closed air channel from the tip of nipple E to the manometer mechanism which is thus isolated from other air channels in the valve chassis. This isolation is desirable since it is desired that meter 12 read pressure in bladder 46 without erratic temporary variations as might result if the meter channel communicated directly with the channel through which air is pumped from bulb 18 into the bladder.

The manometer mechanism includes a bellows 60 which is composed of two half-below sections 60a, 60b secured together around their common circumference. The two half sections of bellows 60 are precisely made to provide a displacement of the free bellows section 60b which is uniformly related to the pressure in channel 54. Desirably, this displacement is lineraly related to the pressure in chamber 54. However, consistent nonlinearities can be corrected by an appropriate mechanical linkage between the sensing pin 62 which sits on free bellows section 60b and indicator 64 (shown in FIG. 1) on the face of the manometer. Various mechanical linkages for converting the small displacement of free bellows section 60b to an appropriate rotational position of indicator 64 are known in the art. The present invention incorporates a linkage arrangement of a type which is well-known in the art manufactured by Propper Manufacturing Company of Long Island City, New York. It is to be understood that each bellows 60 is to some degree unique, and that the manometer must be appropriately calibrated to establish the scale gradations, shown representatively on the face of the manometer in FIG. 1.

As to the external manometer structure, pointer 64 is mounted on a stem 66 which extends into the face of meter 12 to the mechanical linkage arrangement (not shown). Pin 66 passes through a scale plate 68, with pointer 64 being secured to pin 66 after the scale plate is mounted. The entire assembly is adapted to be covered with a transparent crystal 69 usually of glass or plastic. In order to gain access to the linkage mechanism (not shown) crystal 69 must be removed and pointer 64 must be removed from pin 66 so that the scale plate 68 can be removed. Pointer 64 is conventionally removed with a special forceps which is used to grasp the pointer adjacent the wide section where the pointer grasps pin 66. In order to facilitate the grasping and removal of pointer 64, the side surfaces of pointer 64 adjacent pin 66 are flattened so to permit a flat tool to gain secure grasp on the pointer. Conventional meters and pointers include a rounded section of this location and are difficult to securely grasp for removal. In addition, the molded back casing 73 of meter section 12 is shaped as shown in FIG. 1 to include flat sections at the top and sides of the casing to permit the casing to be securely grasped in an appropriate vice or jig as needed during manufacture or repair. Conventional meter casings are circular, making it difficult to retain such casing against rotational or other movement.

As previously described, the use of applicant's sphygmomanometer involves application of a cuff including bladder 46 to the patient's upper arm, inflation of the cuff by repeated squeezing of bulb 18 in the manner previously described with the manometer 12 constantly reading the pressure within bladder 46. As previously indicated, air is then released from the cuff and the systolic and diastolic blood pressures are read on the manometer in accordance with the blood sounds below the cuff. For ease of reading, the cuff pressure is desirably reduced at a constant, relatively slow rate. For this purpose, applicant's preferred embodiment provides a release valve arrangement which permits the doctor to select any one of three different release speeds by depressing the appropriate button A, B or C on the face of the sphygmomanometer, as shown in FIG. 1.

Broadly, this is accomplished by providing a horizontal manifold 70 (best seen in FIG. 8) machined in the chassis 15 of valve section 16 and closed by screw 71 which communicates with chamber 40 (best seen in FIGS. 8 and 4) which in turn communicates through nipple D with bladder 46. The functional arrangement of applicant's release valve system is shown in FIG. 12, wherein it will be apparent that manifold 70 is closed at both ends and communicates with three separate release valves, one associated with each of push buttons A, B and C. Each of the release valves includes a different size aperture (apertures 72a, 72b and 72c) which release air from manifold 70 (and hence from bladder 46) at different rates. Hence when control button B is depressed, for example, the associated valve opens aperture 72b, permitting air to vent to atmosphere and decreasing the pressure in bladder 46 at an approximately controlled rate. It will be appreciated that as the pressure decreases in bladder 46 the rate of pressure decrease decreases through a fixed size aperture. It is thus contemplated that above a certain pressure (for example approximately 90 mm Hg) the slow release button A will be used to provide the desired release rate while below this point the moderate release opening B will be used. The fast release C is provided primarily to permit quick release of the cuff and as a safety valve as discussed hereinafter.

The details of the valve arrangement are shown in FIGS. 6, 7 and 8. The three different sized valve openings 72a, 72b and 72c, associated respectively with buttons A, B and C can best be seen together in FIG. 8. Other than the aperture size, the preferred arrangement of the three valves are substantially identical and are shown representatively in enlarged view in FIG. 7.

FIG. 7 clearly shows manifold 70 and the selected diameter aperture 72 which is normally closed by a closing stud 74, which presses against an O-ring 76. Closing stud 74 includes a forward-protruding narrow pin section 78 which passes completely through aperture 72 and into manifold 70. This pin acts to guide closing stud 74 in its reciprocal movement and simultaneously operates to maintain aperture 74 clear of dust and other debris which might otherwise accumulate and block the aperture. FIG. 7 shows the valve arrangement in its closed position with stud 74 solidly against O-ring 76. To release air through this valve, stud 74 is drawn away from O-ring 76 and air escapes through aperture 72 into the space formerly occupied by stud 74 and through a venting aperture 80 which is provided for each valve.

FIG. 6 shows the stud and O-ring arrangement in combination with the other valve elements for the valve associated with button A.

It will be appreciated that these elements are duplicated for the valves associated with buttons B and C and that the following descriptions of the operation of this valve applies to valves B and C as well. The elements of the valve associated with button A are designated by a number corresponding to the number in FIG. 7, followed by the letter a. Those associated with B are followed by b etc.

Referring to FIG. 6, it will be appreciated that in rest position, the valve is normally retained closed in the following manner: Stud 74a is mounted on a U-shaped bracket 82a by screw 84a. It will be understood that this screw arrangement is only one possible method of securing stud 74 to bracket 82 and that numerous other methods may be employed. For example, the bracket could include an appropriate slot and stud 74 could include a rearwardly intruding prong adapted to be secured within the slot. The U-shaped bracket 82a is secured for reciprocal motion in a forward and rearward direction between the central portion 15a of valve section chassis 15 and a pair of guide posts 83 and 85 which project upwardly from the flat tip of bulb guard member 20. U-shaped support 82a is maintained in the forward direction by a spring 92a positioned on the forward leg of the U-shaped bracket. To open the valve it is only necessary to slide the U-shaped bracket 82a rearwardly until stud 74a releases from O-ring 76a. This is done by button A shown in FIG. 6, which includes a spring 94a which is a relatively light spring adapted merely to keep the button tensed in an outwardly position.

Thus when button A is depressed it abuts the right-hand leg of U-shaped support 82a, driving it toward the left in FIG. 6 (rearwardly) against the urging of spring 92a until stud 74a is released from O-ring 76a, permitting air to vent from manifold 70 through aperture 72a and through vent hole 80a.

As stated previously, the valves associated with B and C are substantially similar to that just described in conjunction with A, except that different sized apertures (72b and 72c) are employed to create a different rate of release for each button (at a given pressure). Each button may be operated independently, with button A releasing air through the relatively narrow aperture 72a and having a slow release rate; button B releasing air through the relatively broader aperture 72b and therefore having a greater but moderate release rate; and button C releasing air through the larger aperture 72c, having a more rapid release rate.

Button A would be used for controlled slow release of air at higher pressures (for example above 90 mm Hg) and B would be used for slow release at lower pressures. Applicants have found that the provision of two constant size apertures operable in high and low ranges leads to more stable slow air release in the hands of the average operator than the continuous turn valves previously used. Button C is used primarily for quick release of air from the cuff, primarily for cuff removal.

In accordance with a preferred embodiment of the present invention, the diameter of aperture 72c and the pressure of the corresponding retaining spring 92c are selected such that the valve associated with button C will function as an emergency release valve when pressure in the bladder manometer system exceeds predetermined levels. With conventional valve arrangements, it is possible to pump bladder 46 up so high that pressure in the bellows 60 is greater than the bellows 60 is designed to accommodate. Under those circumstances, the bellows may become permanently distorted or may even rupture, thereby destroying the accuracy and/or operability of the instrument. To prevent this condition, the spring tension of spring 92c and the size of aperture 72c are selected such that when a selected maximum pressure is reached, the valve automatically opens, preventing further pressurization of the system and damage to the bellows.

FIG. 9 shows the valve associated with button C within its large aperture 72c.

In accordance with a modification of the preferred embodiment described above, one or more of the specific valves may be adapted to establish two specific release rates — one when the related button is depressed slightly, and a second when the related button is depressed more fully. This is accomplished by providing a pin arrangement of the type shown in FIG. 10 includes a narrower forward distal designated 78' in FIG. 10 includes a narrower forward distal section 78'a and a thicker, wider diameter proximal section 78'b. When the button associated with this valve arrangement is depressed slightly, the stud 74' releases from O-rings 76' and releases air to vent opening 80'. However, aperture 72' remains relatively constricted by the broad pin section 78'b, thereby providing a first rate of release for this particular valve. As the associated button is depressed further, pin 78' withdraws more fully until the broad proximal pin section 78'b is fully withdrawn from aperture 72' and the thinner distal pin section 78'a is positioned within aperture 72' providing a relatively more rapid rate of release.

In accordance with a further alternate embodiment of the present invention, one more of the valves may be constructed to provide a continuous variable release rate over a preselected range. This is accomplished by the pinvalve arrangement shown in FIG. 11, wherein the forward pin section now designated 78" is of a continuously varying diameter, such that as the associated button is depressed the rate of release of air increases (at given pressure).

It will be appreciated that with a valve mechanism of the type shown in FIGS. 10 and/or 11, sphygmomanometers can be constructed with fewer than three valves. Obviously, more than three valves could be provided where more release rates are appropriate.

It will also be appreciated that the above described arrangements are merely examples of the application of the present invention and numerous additional embodiments will be apparent to those skilled in the art without departing from the spirit or scope of the present invention as deferred in the appended claims.

What is claimed is:

1. A sphygmomanometer comprising an inflatable cuff of the type adapted to be secured about a patient's limb, an inflation bulb, a one-way output valve in said inflation bulb communicating with said cuff, a one-way input valve in said inflation bulb communicating with atmosphere, a manometer communicating with said cuff for providing a substantially continuous visual indication of the pressure in said cuff, a manifold communicating with said cuff, said manifold including a plurality of apertures of differing diameters, a plurality of closure elements, means mounting each said closure element adjacent a corresponding one of said apertures, each said closure element being individually movable between a closed position wherein air is prevented from escaping from said aperture and an open position wherein air is released from said aperture, spring means associated with each of said closure elements for retaining said closure element in a normally closed position, and a plurality of control buttons, one associated with each closure element for moving said closure element from said closed position to said open position.

2. Apparatus in accordance with claim 1 wherein one of said closure elements includes means to be opened automatically by the pressure in said manifold when the pressure in said manifold reaches a predetermined level so that injury to said manometer is prevented.

3. Apparatus in accordance with claim 1, further including first and second connector nipples, each adapted to receive a flexible rubber tube communicating with said cuff, said first connector nipple communicating with said one-way output valve of said bulb and said manifold, said second nipple communicating with said manometer, so that said manometer is relatively isolated from said bulb and said valves.

4. A sphygmomanometer comprising an inflatable cuff, an inflation bulb, a one-way output valve in said inflation bulb communicating with said cuff, a one-way input valve in said inflation bulb communicating with atmosphere, a manometer communicating with said cuff for providing a visual indication of the pressure in said cuff, a manifold communicating with said cuff, said manifold including a plurality of apertures of different diameters, a plurality of closure elements, one associated with each said aperture, each said closure element including a U-shaped bracket mounted for reciprocating motion adjacent the associated aperture, a closure stud projecting from one of the legs of said U-shaped bracket and adapted to close said aperture when said U-shaped bracked is in a first position and open said aperture when said U-shaped bracket is in a second position, and spring means normally maintaining said U-shaped bracket in said first position, and a plurality of control buttons, one associated with each closure element, for moving said closure element from said first position to said second position.

5. A sphygmomanometer comprising an inflatable cuff, an inflation bulb, a one-way output valve in said inflation bulb communicating with said cuff, a one-way input valve in said inflation bulb communicating with atmosphere, a manometer communicating with said cuff for providing a visual indication of the pressure in said cuff, a manifold communicating with said cuff, said manifold including a plurality of apertures of differing diameters, a plurality of reciprocating closure studs, means mounting each said closure stud adjacent a corresponding one of said apertures, each said closure stud being individually movable between a closed position wherein air is prevented from escaping from said aperture and an open position wherein air is released from said aperture, each such closure stud having a forward extending pin, said pin extending through said aperture when said stud is in said closed position, spring means associated with each closure stud for retaining said closure stud in said closed position, and a plurality of control buttons, one associated with each closure stud for moving said closure stud from said closed position to said open position, at least one of said forward extending pins including at least one section of selected diameter, said at least one section being of a longitudinal extent such that when said closure stud is fully retracted, said at least one section is substantially withdrawn from said aperture, so that each such valve provides at least two distinct release rates at a given pressure.

6. A sphygmomanometer comprising an inflatable cuff, an inflation bulb, a one-way output valve in said inflation bulb communicating with said cuff, a one-way input valve in said inflation bulb communicating with atmosphere, a manometer communicating with said cuff for providing a visual indication of the pressure in said cuff, a manifold communicating with said cuff, said manifold including a plurality of apertures of differing diameters, a plurality of reciprocating closure studs, means mounting each said closure stud adjacent a corresponding one of said apertures, each said closure stud being individually movable between a closed position wherein air is prevented from escaping from said aperture and an open position wherein air is released from said aperture, each such closure stud having a forward extending pin, said pin extending through said aperture when said stud is in said closed position, spring means associated with each closure stud for retaining said closure stud in said closed position, and a plurality of control buttons, one associated with each closure element for moving said closure element from said closed position to said open position, at least one of said forward extending pins being of a varying diameter, so that the rate of release of air through said aperture at a given pressure varies as said pin moves in said aperture.

7. Apparatus in accordance with claim 6 wherein at least one of said pins is of a continuously decreasing diameter.

* * * * *